United States Patent
Kassabgi

(10) Patent No.: US 11,165,723 B2
(45) Date of Patent: Nov. 2, 2021

(54) METHODS AND SYSTEMS FOR A BIMODAL AUTO-RESPONSE MECHANISM FOR MESSAGING APPLICATIONS

(71) Applicant: SENIORLINK INC., Boston, MA (US)

(72) Inventor: George Kassabgi, Winchester, MA (US)

(73) Assignee: SENIORLINK INC., Boston, MA (US)

( * ) Notice: Subject to any disclaimer, the term of this patent is extended or adjusted under 35 U.S.C. 154(b) by 160 days.

(21) Appl. No.: 15/935,673

(22) Filed: Mar. 26, 2018

(65) Prior Publication Data

US 2018/0278554 A1    Sep. 27, 2018

Related U.S. Application Data

(60) Provisional application No. 62/476,966, filed on Mar. 27, 2017.

(51) Int. Cl.
| | |
|---|---|
| *H04L 12/58* | (2006.01) |
| *G16H 80/00* | (2018.01) |
| *G16H 50/70* | (2018.01) |
| *G16H 40/63* | (2018.01) |
| *G16H 50/20* | (2018.01) |
| *G16H 10/20* | (2018.01) |

(Continued)

(52) U.S. Cl.
CPC ............ *H04L 51/02* (2013.01); *G06F 40/279* (2020.01); *G06F 40/30* (2020.01); *G06F 40/35* (2020.01); *G06F 40/56* (2020.01); *G16H 10/20* (2018.01); *G16H 40/63* (2018.01); *G16H 50/20* (2018.01); *G16H 50/70* (2018.01); *G16H 80/00* (2018.01); *G06N 20/00* (2019.01); *H04L 51/32* (2013.01); *H04L 51/38* (2013.01)

(58) Field of Classification Search
CPC ........ G06F 40/279; G06F 40/30; G06F 40/35; G06F 40/56; G06N 20/00; G06N 5/047; G06N 7/005; G16H 10/20; G16H 40/63; G16H 50/20; G16H 50/70; G16H 80/00; H04L 51/02; H04L 51/32; H04L 51/38
See application file for complete search history.

(56) References Cited

U.S. PATENT DOCUMENTS 10,120,859 B2 * 11/2018 Parikh .................... H04L 51/02
11,011,160 B1 *  5/2021 Villaizan ............... G10L 15/187
(Continued)

*Primary Examiner* — Philip J Chea
*Assistant Examiner* — Ruth Solomon
(74) *Attorney, Agent, or Firm* — Lando & Anastasi, LLP

(57) ABSTRACT

Systems and methods of automatically generating a proposed response to user input are provided. A method includes receiving, via a text-based messaging system, a plurality of messages from a user, determining a respective confidence level for each message of the plurality of messages that the respective message has a respective intent corresponding to a respective defined intent, generating, responsive to the defined intent of a first message of the plurality of messages being a structured intent, a first proposed communication from the structured intent, and generating, responsive to the defined intent of a second message of the plurality of messages being a predictive intent and the confidence level of the second message meeting a defined threshold, a second proposed communication from the predictive intent.

18 Claims, 4 Drawing Sheets

(51) Int. Cl.
    *G06F 40/30*     (2020.01)
    *G06F 40/35*     (2020.01)
    *G06F 40/56*     (2020.01)
    *G06F 40/279*     (2020.01)
    *G06N 20/00*     (2019.01)

(56) References Cited

U.S. PATENT DOCUMENTS

| | | | |
|---|---|---|---|
| 2014/0337048 A1* | 11/2014 | Brown | G10L 15/08 705/2 |
| 2015/0178371 A1* | 6/2015 | Seth | G06Q 30/02 707/748 |
| 2016/0218997 A1* | 7/2016 | Patil | G06F 40/274 |
| 2018/0089163 A1* | 3/2018 | Ben Ami | H04L 51/02 |
| 2018/0131645 A1* | 5/2018 | Magliozzi | G06Q 10/107 |
| 2018/0174055 A1* | 6/2018 | Tirumale | G06N 5/02 |
| 2018/0232662 A1* | 8/2018 | Solomon | G06K 9/6255 |
| 2018/0261203 A1* | 9/2018 | Zoller | G06Q 50/01 |

* cited by examiner

| | System | User |
|---|---|---|
| 1 | How is John doing? | |
| 2 | | He's okay. Do you know if we're supposed to get snow soon? |
| 3 | Yes. We are forecast to receive 3" of snow on Tuesday. | |
| 4 | | Okay, thanks. I worry about him slipping. |
| 5 | Would you like to take a quick fall risk screener for John? | |
| 6 | | Sure. |
| 7 | Has John fallen in the past year? | |
| 8 | | I don't think so. |
| 9 | Are there times when John feels like he doesn't have his balance? | |
| 10 | | Only when it's slippery. Do you think it will be icy on Tuesday night? |
| 11 | The forecast says there will be a low of 20 degrees, with clear skies. | |
| 12 | | Okay, thanks. |
| 13 | You're welcome. | |
| 14 | | Sorry, what were you going to ask me? |
| 15 | Does John have concerns about falling? | |
| 16 | | I don't think so. |
| 17 | John's fall risk is low, but I can send you an email with some additional information if you like? | |
| 18 | | Yes, please. |

FIG. 3

METHODS AND SYSTEMS FOR A BIMODAL AUTO-RESPONSE MECHANISM FOR MESSAGING APPLICATIONS

CROSS-REFERENCE TO RELATED APPLICATIONS

This application claims priority to U.S. Provisional Application Ser. No. 62/476,966, titled "METHODS AND SYSTEMS FOR A BIMODAL AUTO-RESPONSE MECHANISM FOR MESSAGING APPLICATIONS," filed on Mar. 27, 2017, which is incorporated herein by reference in its entirety.

BACKGROUND

Technical Field

The application generally relates to messaging applications, and more particularly, in one aspect, to systems and methods for automatically generating responses to user input.

Background

Much of society's interpersonal communication has shifted from face-to-face meetings or telephone discussions to electronic communication, such as email, SMS messaging, or other messaging formats. Such asynchronous forms of communication allow for conversations to be conducted at the convenience of each party, and may be carried on in parallel with a number of other users.

For those reasons, online messaging has proven useful for facilitating expert-consumer interactions. Such interactions often involve a subject matter expert conversing with a consumer of a good or service to diagnose and address problems, and to address any questions the consumer may have. For example, an ecommerce customer service representative may help an ecommerce consumer to resolve an issue with a purchased product, or an insurance agent may assist a customer with selecting or modifying an insurance policy. Online messaging also allows for sharing images, videos, documents, and other files, allowing for more effective discussion and collaboration than voice calls.

Expert-consumer interactions also occur in the field of medical case management. Thus, online messaging has been implemented as a replacement to telephone communications in medical case management. Telephone communication has drawbacks. It is estimated that a case manager (e.g., a nurse or physician's assistant) attempting to reach a caregiver or patient by phone is able to reach and speak with the other party only about 30% of the time, meaning a majority of time is spent playing "phone tag." Even when a connection is made, one of the parties may mishear critical information due to a bad connection or distraction. The parties must also remember (or write down) any relevant information received during the call. Retention may be an issue, and if the information must later be conveyed to someone else, additional misunderstanding or misinterpretations may arise.

Messaging between experts and consumers is known. For example, in the medical context, case managers may communicate with caregivers of patients in their caseload by manually typing messages using SMS messaging or other messaging formats. Yet there are a number of drawbacks to this approach. First, the case manager may be caring for many patients, leading to delayed responses from the case manager in response to a caregiver's questions or concerns.

The number of patients in the caseload may also cause the case manager to lose track of the various threads of conversation. The case manager may also be required to repeatedly pose the same series of questions to different patients (e.g., going through a fall risk assessment with the caregiver for each patient). If the caregiver changes the subject mid-assessment, the case manager may forget to return to it at a later time, leading to an incomplete assessment. Finally, the Health Insurance Portability and Accountability Act of 1996 (HIPAA) disallows the transmission of sensitive medical information over unsecure communication formats, such as SMS.

Unimodal auto-response systems are known. Such systems fall into one of two categories. The first category includes predictive systems, in which the system responds to discrete user queries or messages based primarily on probability from a training dataset. Currently available predictive systems do not store or exploit longitudinal data relating to the user or others. They also do not provide for a conversational flow that follows a pathway, such as a series or decision tree of questions or other interactions with the user. The second category includes structured systems, in which a deterministic (as opposed to probabilistic) system can guide the user through a series of questions and receive an expected answer. Such structured systems are not configured to handle ad-hoc or unexpected comments or questions from the user.

SUMMARY OF THE INVENTION

The presently disclosed systems and methods address the drawbacks of current messaging systems by providing a bimodal auto-response system (sometimes called a "chatbot") for responding to messages from users, including by using longitudinal data. In particular, a bimodal auto-response system is employed, with the system switching between a structured mode and a predictive (i.e., unstructured) mode depending on the nature of the messages received from the user. For example, the system may process user messages in the predictive mode, until it is determined that the user's message calls for a structured exchange.

While automated response systems are known, current systems are unimodal, configured to operate in either a structured mode or a predictive mode. Known predictive systems are also typically "stateless," being unable to store longitudinal information for use later. The currently disclosed bimodal systems and methods offer an improved solution, including for applications involving expert-consumer interactions. Conversations and screenings can be carried out by the system with minimal involvement or oversight from the subject matter expert. If the system cannot determine, to a certain confidence level, the user's intent from a message, a proposed response may be generated and sent or displayed to the subject matter expert. If the auto-generated response is suitable, the subject matter expert may approve the message to be sent to the consumer. If not, the message may be rejected. Either way, machine learning can be applied to the subject matter expert's treatment and/or modification of the communication to improve future proposed communications.

To give an example in the medical context, the auto-response system may be communicating with the caregiver of a patient in a predictive (i.e., unstructured) mode, responding to queries and making general inquiries as to the patient's well-being. The system may then detect that one of the caregiver's messages relates to the patient falling—for example, by reporting a fall incident, or simply expressing concern that the patient may fall. Upon detecting such an intent in the user's message, the system may offer to perform a standard "fall risk screener," in which the system poses a series of questions about the patient to the caregiver, such as the patient's age (if not known), the patient's number of falls in the previous year, etc. If the caregiver agrees, the system automatically switches to a structured mode by beginning to ask, in an orderly manner, the questions in the screener.

If a caregiver's message in response to such a structured question veers off topic (e.g., by asking an unrelated question or offering unrelated information), the system may switch back to the predictive mode in order to address the caregiver's message. Meanwhile, the current state of the structured mode (e.g., the position in, and responses to, the fall risk screener) may be stored in a reentrant stack. At some point in the future—such as after a certain amount of time has passed, or when the conversation returns to a topic related to the patient's balance or fall risk—the system may switch back to the structured mode, attempting to elicit the information not yet provided in the interrupted screener.

Conducting such routines conversations with automated responses reduces the amount of time a human case manager (e.g., a nurse) need be involved in crafting responses. This, in turn, allows the case manager to take on a larger case load.

By shifting control between a predictive mode and a structured mode, the auto-response system is able to engage with the user (e.g., a caregiver) about general topics or topics of the user's choice, while at the same time switching to the structured mode for a more structured question-and-answer flow when appropriate. What's more, the system stores and/or retrieves longitudinal information, so is able to take that information into account when generating messages. Longitudinal data may be obtained and used in either the predictive mode or the structured mode. In particular, longitudinal data may be referenced or used in a predictive pattern in the predictive mode, or in a rule or a response to the user in either the predictive mode or the structured mode. As a simple example in the medical context, the system may learn the patient's name, so is able to refer to the patient by name in its messages (e.g., "How is John doing?"). As another example, the system may learn the patient's date of birth, and so does not need to ask for that information, such as when conducting a structured screening or other conversation that ordinarily calls for such information.

The system may be configured to communicate with any number of data sources to retrieve requested or necessary information for conversing with the user, including through the use of Application Programming Interfaces (APIs). Such data sources may include the patient's electronic medical file, medical encyclopedias or databases, drug or medication information, or general data sources.

Accordingly, the system is able to provide many of the benefits of person-to-person conversation while simultaneously providing benefits which are unattainable with person-to-person conversation. The system's ability to store information conveyed by the patient, and subsequently refer to the patient's entire medical history when generating responses to the patient, enables a level of omniscience which is unattainable by a human doctor. The system may therefore provide several advantages to address problems which many be inherent to direct doctor-to-patient communication, including forgetting medical history information, misunderstanding information conveyed by a patient, inaccurately transcribing information provided by a patient, incorrectly or incompletely conveying information to other medical personnel (e.g., during shift changes), becoming distracted during a diagnostic screening and forgetting which step of the diagnostic screening the doctor was at prior to the distraction, and so forth.

According to one aspect, a method of automatically generating a proposed response to user input includes acts of receiving, via a text-based messaging system, a plurality of messages from a user, determining a respective confidence level for each message of the plurality of messages that the respective message has a respective intent corresponding to a respective defined intent, generating, responsive to the defined intent of a first message of the plurality of messages being a structured intent, a first proposed communication from the structured intent, and generating, responsive to the defined intent of a second message of the plurality of messages being a predictive intent and the confidence level of the second message meeting a defined threshold, a second proposed communication from the predictive intent.

In one embodiment, the method further includes, responsive to a defined intent of a respective message being a predictive intent, storing a state of a respective structured intent, generating a respective proposed communication from the predictive intent, and responsive to detecting a triggering event, restoring the state of the respective structured intent and generating a proposed communication from the respective structured intent. In some embodiments, detecting the triggering event is one of determining that a predetermined amount of time has passed, determining that a respective message has an intent corresponding to a topic, and determining that the respective message has an intent corresponding to the structured intent.

In some embodiments, generating the first proposed communication from the structured intent comprises identifying a piece of information required by the structured intent, and responsive to determining that the piece of information has not previously been provided, generating the first proposed communication to request the piece of information from the user. In an embodiment, the method includes generating, responsive to the defined intent of a third message of the plurality of messages being a predictive intent and the respective confidence level not meeting a defined threshold, a third proposed communication from the predictive intent and presenting the third proposed communication to a second user of the system.

In an embodiment, the method includes receiving, from the second user, one of a first instruction to accept the third proposed communication and a second instruction to reject the third proposed communication. In some embodiments, the user is a consumer, and the second user has expertise in a subject matter relevant to the consumer. In at least one embodiment, the user is a caregiver to a patient, the second user is a medical professional, and the third proposed communication relates to care of the patient. In some embodiments, the user is one of a patient and a caregiver to a patient, and wherein the structured intent defines at least one clinical pathway for making a determination about the patient's health.

In one embodiment, the method includes transmitting the first proposed communication and the second proposed communication to the user. In an embodiment, the text-based messaging system comprises one of a native messaging application, a secure messaging application, a messaging application associated with a social media platform, and an SMS messaging application. In some embodiments, determining the confidence level that a respective message has an intent corresponding to the defined intent is performed using at least one of a text-pattern matching process, a classification algorithm, and a neural network. In at least one embodiment, the method further includes determining, from a respective message, a piece of information about the user, and storing the piece of information about the user in one of a state machine and persistent storage.

According to one aspect, a bimodal auto-response system is provided including an intent processor storing at least one structured intent and at least one predictive intent, a state machine storing at least one piece of information about a topic, a network interface configured to receive, over a communication network, a message from a user, a predictive text classifier configured to determine a confidence level that the intent corresponds to at least one intent of the at least one structured intent and the at least one predictive intent, and a rules engine configured to generate a proposed communication from the at least one intent.

In one embodiment, the system includes an API interface configured to receive information from at least one data source other than the state machine. In some embodiments, the topic is a patient, and the at least one piece of information comprises longitudinal data about the patient. In at least one embodiment, the intent processor further comprises a reentrant stack configured to store a state of at least one structured intent. In some embodiments, the predictive text classifier is further configured to identify at least one part of speech in the message.

According to one aspect, a method of automatically generating a proposed response to user input is provided. The method includes receiving, via a text-based messaging system, a message from a user; determining a confidence level that the message has an intent corresponding to a defined intent; responsive to the defined intent being a structured intent, generating a proposed communication from the structured intent; and responsive to the defined intent being a predictive intent and the confidence level meeting a defined threshold, generating the proposed communication from the predictive intent.

According to one embodiment, the method includes, responsive to the defined intent being a predictive intent, storing a state of a structured intent; generating the proposed communication from the predictive intent; and responsive to detecting a triggering event, restoring the state of the structured intent and generating a proposed communication from the structured intent. According to another embodiment, detecting the triggering event is one of determining that a predetermined amount of time has passed, determining that the message has an intent corresponding to a topic, and determining that the message has an intent corresponding to the structured intent. According to yet another embodiment, generating the proposed response from the structured intent includes identifying a piece of information required by the structured intent; and responsive to determining that the piece of information has not previously been provided, generating the proposed communication to request the piece of information from the user.

According to another embodiment, the method includes, responsive to the defined intent being a predictive intent and the confidence level not meeting a defined threshold, presenting the proposed communication from the predictive intent to a second user of the system. According to a further embodiment, the method includes receiving, from the second user, one of a first instruction to accept the proposed communication and a second instruction to reject the proposed communication. According to a still further embodiment, the user is a consumer, and the second user has expertise in a subject matter relevant to the consumer. According to yet a further embodiment, the user is a caregiver to a patient, the second user is a medical professional, and the proposed communication relates to care of the patient.

According to one embodiment, the user is one of a patient and a caregiver to a patient, and the structured intent defines at least one clinical pathway for making a determination about the patient's health. According to another embodiment, the method further includes transmitting the proposed communication to the user. According to a still further embodiment, the text-based messaging system includes one of a native messaging application, a secure messaging application, and an SMS messaging application. According to another embodiment, determining the confidence level that the message has an intent corresponding to the defined intent is performed using at least one of a text-pattern matching process, a classification algorithm, and a neural network. According to yet another embodiment, the method includes determining, from the message, a piece of information about the user; and storing the piece of information about the user in a state machine.

According to another aspect, a bimodal auto-response system is provided. The system includes an intent processor storing at least one structured intent and at least one predictive intent; a state machine storing at least one piece of information about a topic; a network interface configured to receive, over a communication network, a message from a user; a predictive text classifier configured to determine a confidence level that the intent corresponds to at least one intent of the at least one structured intent and the at least one predictive intent; and a rules engine configured to generate a proposed communication from the at least one intent.

According to one embodiment, the system further includes an API interface configured to receive information from at least one data source other than the state machine. According to another embodiment, the topic is a patient, and the at least one piece of information comprises longitudinal data about the patient. According to yet another embodiment, the intent processor further comprises a reentrant stack configured to store a state of at least one structured intent. According to another embodiment, the predictive text classifier is further configured to identify at least one part of speech in the message.

Still other aspects, embodiments, and advantages of these exemplary aspects and embodiments are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment," or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral.

For purposes of clarity, not every component may be labeled in every figure. In the figures:

FIG. 3 is an exemplary transcript of a conversation between a user and an auto-response system according to some embodiments.

DETAILED DESCRIPTION

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Figure 1:
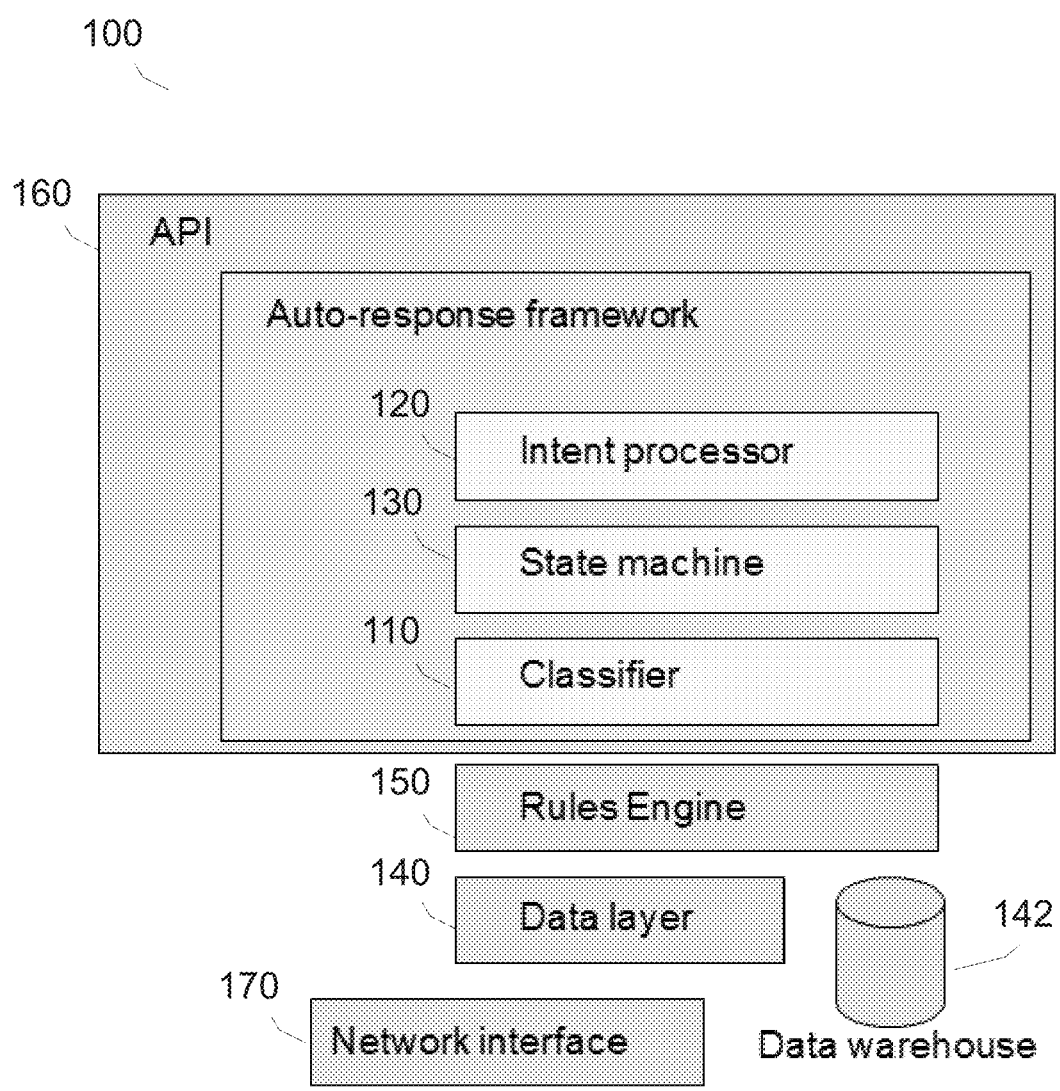
FIG. 1 is a block diagram of a computer system for providing a bimodal auto-response mechanism for messaging applications according to some embodiments.

FIG. 1 is a block diagram of a system 100 configured to provide a bimodal auto-response mechanism for messaging applications. A predictive text classifier 110 contains definitions for processing and classifying messages from a user (i.e., a consumer in an expert-consumer relationship) and determining (e.g., from their parts of speech or structure) a probability that the user's message relates to one or more defined "intents."

An intent processor 120 loads and processes a number of defined intents that define, for a particular input and/or a class of inputs, a set of acceptable responses. The intent processor 120 defines both predictive (i.e. open-ended) intents and structured intents. The intent processor 120 may employ a reentrant stack that allows it to store and persist, for a particular user, a current state of one or more defined intents, and to restore the state later. For example, when the state of a first structured intent is stored, the system 100 may subsequently process other intents in response to user input, then restore the state when the first structured intent is resumed at a later time. A state machine 130 is provided that maintains a state of the user session (or previous sessions), and may do so by using a data structure such as a data dictionary.

The system 100 includes a network interface 170 configured to communicate with a user via a network by sending and receiving messages (e.g., SMS messages or messages within a messaging application on a mobile device or personal computer). A rules engine 150 processes the message by communicating with the predictive text classifier 110, the intent processor 120, and/or the state machine 130 to predict the user's intent, access necessary state and/or user information, and determine an appropriate response to the user's message. If the user's message relates to a predefined structured intent, that structured intent (including any questions or information defined therein) may be used to generate response. If the user's message does not relate to a structured intent, then a predictive intent will be used if there is above a threshold probability that the predictive intent matches the user's intent.

The rules engine 150 may access a data layer 140, which may include or be otherwise coupled to a data warehouse 142, that stores longitudinal data about the patient. The predictive text classifier 110, the intent processor 120, and/or the state machine 130 may be packaged as a service, for example, as an Application Programming Interface (API) 160. The rules engine 150 may access those components by making calls to the API 160.

The predictive text classifier 110 may classify a message from the user according to the likelihood that the message relates to a certain intent or meaning of the user. For example, the predictive text classifier 110 may identify concepts in the message, and create a structured text object that contains the concepts. The predictive text classifier 110 then applies statistical information to the structured text object in order to calculate a set of match scores, each match score representing the relevance of the text to an associated one of a plurality of predefined categories. In addition to concepts, information used by the predictive text classifier 110 in calculating match scores may include the use of passive voice, semantic information, contextual information, morphological information, and quantitative information. The quantitative information may include the number of sentences or number of exclamation points. Other aspects of the message that are examined may include sentences, phrases, words, stems, semantically significant constructs, the type and number of punctuation marks, strong use of the passive voice, and dates.

To give an example, a user message "what's the weather going to be like today?" may be classified by the predictive text classifier 110 as having a very high probability of relating to a defined intent for responding with the weather forecast for that day. A user message "should I wear a jacket today?" may also be classified as having a somewhat high probability of relating to the weather forecast for that day, but may have a relatively lower probability than the previous example, as the user here may also be referring to an event for which a suit jacket may be required. The predictive text classifier 110 may match the message from the user with a predefined intent that has been manually defined by a system operator, or may use machine learning or other techniques to determine the user's intent. In some embodiments, the predictive text classifier 110 may employ part-of-speech tagging to aid in determining the user's intent. In particular, a part-of-speech tagger may be incorporated or accessed that reads text and assigns parts of speech to each word, such as "noun," "verb," "personal pronoun," etc.

The intent processor 120 loads a number of defined intents (e.g., from a file or a memory), which are used to determine an appropriate response to a user's message. Each intent may have a tag or label that may be used to identify or call it. Each intent may also define one or more patterns for user messages that may relate to the intent, as well as one or more responses to user messages determined to match that intent.

An exemplary predictive intent tagged "human" is shown below. This "human" intent is to be used when a user message inquires or relates to whether the auto-response system is in fact a human:

```
{"tag": "human",
    "patterns": [
        "are you a robot",
        "are you human",
        "what are you",
        "are you real",
        "are you a real person",
        "are you like Siri",
        "do you have a heart"
    ],
    "responses": [
        {"order": 0,
            "condition": "True",
            "replies": [
                "I am here to help",
                "What is real?",
                "I have a big heart"
            ]
        }
    ]
}
```

A number of patterns for the expected message matching this intent are defined, such as "are you a robot," "are you human," "what are you," "are you real," and so forth. Similarly, a number of responses to messages matching these patterns (i.e., this intent) are defined, including "I am here to help" and "What is real?" A response is selected from among the possible responses at random to avoid repetition.

Structured intents may also be defined. A structured intent may include a set and/or sequence of questions to be asked of the user in response to a message matching one or more patterns, with the user's messages in response used to control or modify the logical flow through the structured intent. For example, the structured intent may define a questionnaire, a survey, or a battery of test questions to be posed to the user. In an example in the medical context, where the user is a caregiver and the auto-response system is conversing with the user regarding a patient of the caregiver, the structured intent may define a diagnostic questionnaire, a health or risk screening, an intake questionnaire, or other form in which medical professionals communicate with patients and/or their caregivers.

To give an example, a "fall risk" structured intent may be defined and used in response to a user (e.g., a caregiver) sending a message about the patient falling, tripping, or having balance issues. The structured intent may be designed to send the caregiver a series of questions constituting a fall risk screener. For example, the caregiver may be asked about the patient's age (if not already known); the number of falls by the patient in the previous year; the patient's sense of balance; and the patient's concerns about falling. The caregiver's responses to these questions may be used by the structured intent to evaluate the patient's fall risk. Depending on the outcome, the response to the caregiver may include a level of the patient's fall risk (e.g., high, medium, or low), and may include additional information (or links thereto) about the risk.

Referring still to FIG. 1, the state of one or more intents may be stored by the state machine 130. This stored state allows the system to switch between a predictive mode and a structured mode in response to user messages. In this manner, for example, a series of questions in a structured intent may be interrupted when a message from the user relates instead to a predictive intent. In that case, the state machine 130 stores the current state of the structured intent, and yields control of the auto-response system to the predictive mode in order to address the user's current message. The stored state may include the questions and answers already posed and answered, as well as any information relevant to the structured intent and already determined from other sources. When the structured intent is resumed later, the state is restored, and the structured intent continues from an appropriate place.

To continue the previous example, the fall risk screener may be in process when the user sends a message asking when the patient's next medical appointment is. In response, the state machine 130 stores the current state of the fall risk screener (including what questions have been asked, and the response, if any, to those questions). Control of the auto-response system then yields to the predictive mode, and the question about the medical appointment (and any follow-up and/or subsequent questions) is answered to the best of the system's ability. When the fall risk screener is resumed at a later time, the state stored in the state machine 130 for that structured intent is restored. Already answered questions may not be repeated, with the fall risk screener simply picking up where it left off.

During operation, the rules engine 150 processes messages from the user by passing them to the predictive text classifier 110 and/or the intent processor 120. The data layer 140 may be used to access longitudinal data about the user and/or others (e.g., a patient of a user-caregiver in a medical context). Longitudinal data may include information about the user, or the user's prior interactions or transactions with the system or related entities.

In the medical context, such longitudinal data may include biographical data (such as the patient's name, age/date of birth, gender, or race) or medical/physiological data (the patient's height, weight, medical history, current condition, health risks). In some embodiments, the patient's electronic medical records may be accessed and/or stored in the data layer 140. Information in the data layer 140 may be used to control the responses from one or more intents. For example, a response to a predictive intent may incorporate the user's name (e.g., "bring your umbrella today, Jim."). As another example, information typically requested in a structured intent may not be requested if already accessible in the data layer 140. For example, if a patient's age is part of a diagnostic questionnaire, but the patient's date of birth is already stored in the data layer 140, the patient's age will not be asked.

System 100 may be used to process user input according to a predictive mode or a structured mode, depending on the nature of the user input. The predictive mode may operate until a user response (such as a message about a particular topic) causes control to switch to the structured mode, which may begin asking a series of questions in a relevant structured intent. A user's response (or lack thereof) to a question may cause the state of the structured mode to be saved, and control to switch back to the predictive mode. After some amount of time or a triggering event (such as receiving a user message asking "what were we talking about?" or detecting that the user has begun making "small talk"), control may again be given to the structured mode, with the state of the interrupted structured intent being restored.

Figure 2:
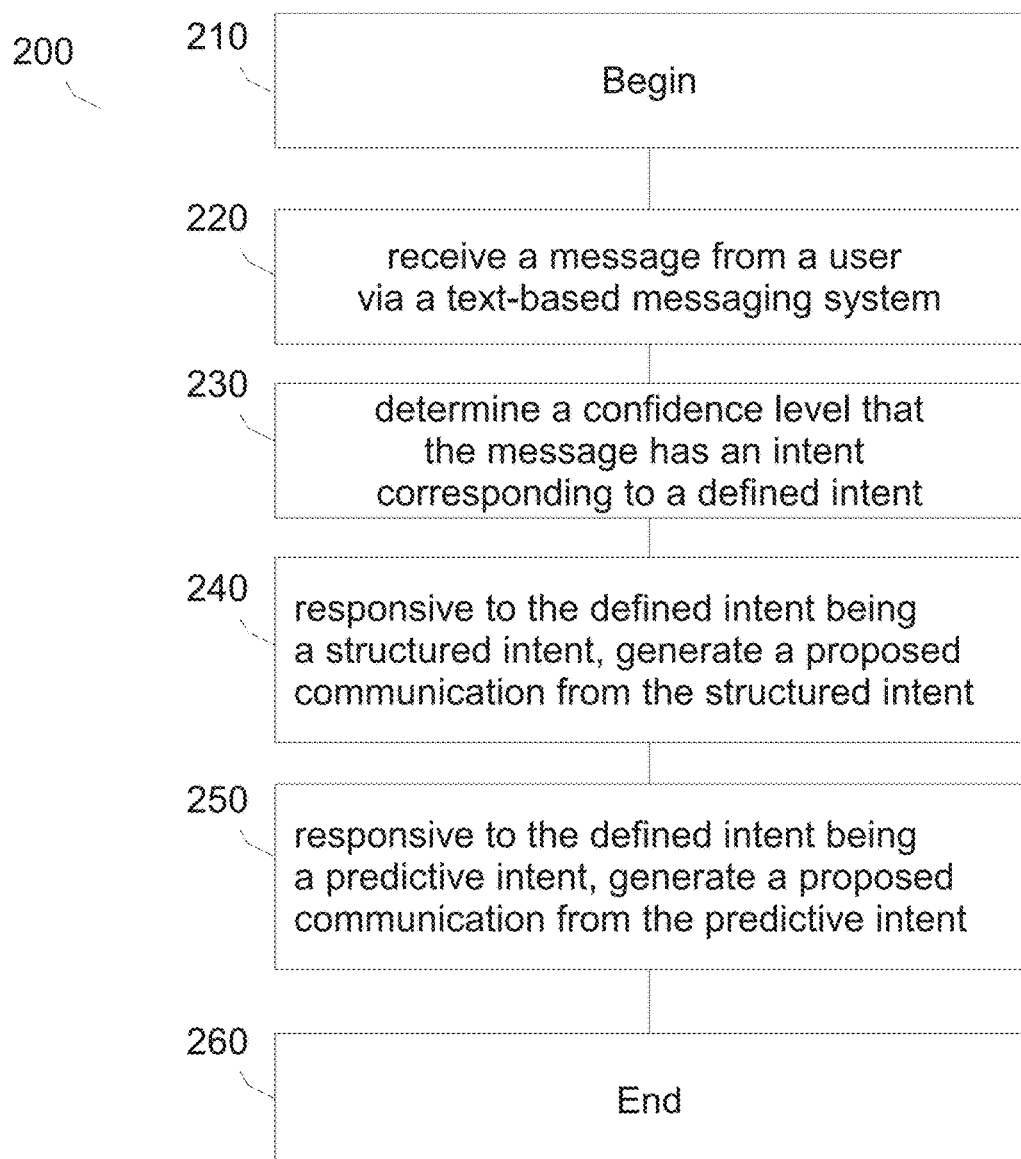
FIG. 2 is a flow diagram of one example process for providing a bimodal auto-response mechanism according to some embodiments.

FIG. 2 shows an exemplary method 200 of automatically generating a proposed response to user input according to some embodiments.

At step 210, method 200 begins.

At step 220, a message is received from a user via a text-based messaging system. The messaging system may be an SMS messaging system, or may be a dedicated messaging application. In some embodiments, a secure messaging application may be used, particular where privacy (e.g., in a medical setting) is desired, or required by law. The message may be received via a network interface by a processor (e.g., the rules engine 150 of FIG. 1) running as a service and/or on the cloud. In some embodiments, the message may be received via a social media application, such as the Facebook application offered by Facebook, Inc. of Menlo Park, Calif.

At step 230, a confidence level is determined that the message has an intent corresponding to a defined intent. In some embodiments, where a number of defined intents are provided, a confidence level is determined for each defined intent. The defined intent having the highest confidence level may be identified as the most probable intent of the user. The confidence level for each defined intent may be determined through one or more of pattern matching, classification algorithm (including part-of-speech classification), machine learning, neural networks, or other techniques.

At step 240, responsive to the defined intent being a structured intent, a proposed communication is generated from the structured intent, and at step 250, responsive to the defined intent being a predictive intent and the confidence level meeting a defined threshold, the proposed communication is generated from the predictive intent. In a preferred embodiment, if a structured intent matches the user's determined intent above a certain threshold, a proposed response will be generated from that structured intent. (In some embodiments, a structured intent having a confidence level over the threshold may be used even where a predictive intent has the same or higher confidence level.) On the other hand, if the defined intent best matching the user's determined intent is a predictive intent, the confidence level in the match will be considered. If the system is reasonably certain, above a certain threshold, that the defined predictive intent matches the user's intent, a proposed response will be generated from that predictive intent. If the certainty falls below the threshold, the system may escalate to involve a human operator (as described below), may inform the user that the message was not understood, and/or may ask one or more additional questions to attempt to determine the user's intent with greater confidence.

Steps 210-250 may be repeated any number of times during an interaction, and with each pass, control can shift between a predictive mode and a structured mode at steps 240 and 250. In some embodiments, the proposed communication generated in step 240 or 250 may be presented to a human operator for approval if the confidence level that the user's intent has been properly identified falls below a certain threshold. The threshold may be set manually, or may be determined automatically (or partially automatically) based on one or more factors, including the system's experience with a particular concept being discussed with the user, or the risks associated with a particular concept being discussed with the user. In one example in the medical context, a higher threshold of certainty may be required when conversing with a user about heart attack symptoms than about a minor skin condition. The threshold may also be set or adjusted according to staffing levels or, relatedly, the time of day or day of the week that the proposed communication is generated. For example, human review may be delayed for a proposed communication generated during the weekend or at night, due to reduced staffing or staff unavailability due to sleep schedules. A lower threshold may accordingly be set for some proposed communications (e.g., those relating to topics involving a relatively low amount of risk) generated during those "off hours," to allow the system to send proposed communications that under other circumstances would have been reviewed by a human due to a higher threshold setting. To give an example in the medical context, the system may determine, to a certain confidence level, that a user's question is about a minor skin condition. During normal business hours, that confidence level may be low enough to require that a human operator review the proposed communication. During off-hours, however, the same confidence level for a question about such a low-risk condition may be deemed sufficient to generate and send the proposed communication without involvement of a human operator.

If the human operator determines that the proposed communication is appropriate, the human operator may be provided the ability (e.g., with a user interface element) to approve the communication, causing it to be sent to the user. If, on the other hand, the human operator determines that the message is not appropriate, the human operator may be provided the ability to reject the communication, to modify the communication, or to write a new communication in place of the proposed communication. Machine learning can be applied to the human operator's treatment and/or modification of the communication to improve future proposed communications.

In any event, the system may then wait for another message from the user, or may take some action after a certain time, or after a certain amount of inactivity. For example, the system may terminate the conversation, or may ask if the user would still like to converse.

At step 260, method 200 ends.

Once the proposed communication has been generated and/or approved, it may be sent to the user. In some embodiments, the timing or format of the message may be set to more closely approximate human interaction. For example, even though the proposed communication can be generated and sent nearly instantaneously, a delay may be observed before sending the response, to simulate the time it would take a human to craft and send a communication. The system may also use the user's name and/or the patient's name periodically to establish a rapport.

The system may return control to the structured mode, or attempt to do so, in response to one or more triggering events or conditions. For example, the system may periodically (e.g., once a month) prompt the user to take a wellness screening for the patient. If the user agrees, a structured intent for such a screening may be used. As another example, where a structured intent has been interrupted and control has been returned to the predictive mode, the user may be prompted to return to the structured intent (i.e., the structured mode). Such prompting may occur, for example, when the user has fallen silent for some amount of time, or after a certain amount of time (e.g., an hour). As another example, the context of the user's message may indicate a desire or willingness to return to the structured intent. For example, a message from the user may relate to the subject matter of a previous structured intent, indicating a desire to return control to that structured intent. Similarly, a message from the user asking for an earlier question to be repeated, asking for a reminder as to what the conversation is about, apologizing for going off track, or engaging in small talk may be interpreted by the system as a desire to return control to the structured mode.

An exemplary conversation 300 in which the auto-response system shifts between a predictive mode and a structured mode to communicate with a user (i.e., a caregiver) in a medical context can be seen in FIG. 3.

At lines 1-4, the system is in a predictive mode. Messages from the user are received and text-classified to identify any concepts within, and the concepts are compared to the defined intents to determine a proposed response. For the response at line 3, for example, the system has determined that the user is asking about the weather forecast (specifically, precipitation) for Tuesday, and has accessed a database (e.g., an external weather forecast database) for information to be used in generating the proposed response. At line 4, the system has determined that the user's comment about the patient slipping matches the "fall risk" intent referred to above. In response, the system asks if the user would like to take a fall risk screener.

When the user agrees to the fall risk screener, the system shifts to a structured mode, as seen at line 7. Notably, though the fall risk screener typically takes into account a patient's age, the system in this example has previously determined and stored the patient's age, which may have been provided in the patient's medical record, or in an earlier discussion with the user. Thus, the system moves directly onto another question in line 7, namely, whether the patient has fallen in the past year. At line 8, the user provides an answer, and at line 9, the user asks another question in the fall risk screener. At line 10, however, the user answers the question ("only when it's slippery") but then relatedly asks the system whether it will be icy on Tuesday night.

In response, the system saves the state of the "fall risk" structured intent, and switches to a predictive mode by answering the user's question about the weather on Tuesday night at line 11. At line 12, the user asks the system a question that triggers a transfer of control back to the structured mode. The state of the structured intent relating to the fall risk screener is restored, and the system resumes the screener at the next question in line 15.

In response to the user's responses to the fall risk screener, the system provides an assessment at line 17, and offers additional information.

It will be appreciated that the specific examples given herein relate to a medical context generally, and a case manager-caregiver relationship in particular, for consistency and ease of illustration only. The methods and systems described here are equally applicable to any automatic messaging system, and to any online interactions, including those embodying other expert-consumer relationships.

Figure 4:
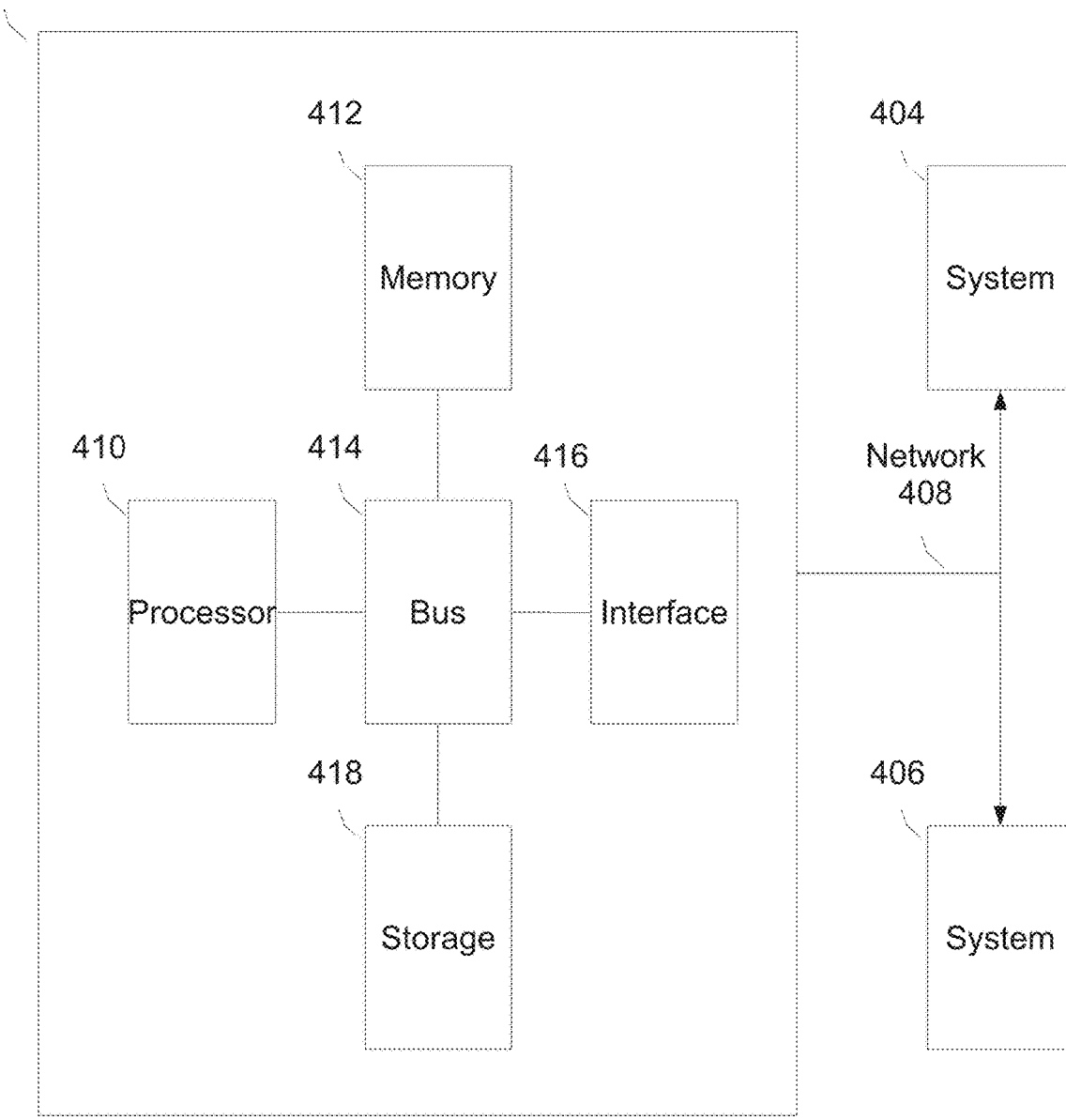
FIG. 4 is a block diagram of one example of a computer system on which aspects and embodiments of this disclosure may be implemented.

FIG. 4 is a block diagram of a distributed computer system 400, in which various aspects and functions discussed above may be practiced. The distributed computer system 400 may include one or more computer systems. For example, as illustrated, the distributed computer system 400 includes three computer systems 402, 404 and 406. As shown, the computer systems 402, 404 and 406 are interconnected by, and may exchange data through, a communication network 408. The network 408 may include any communication network through which computer systems may exchange data. To exchange data via the network 408, the computer systems 402, 404, and 406 and the network 408 may use various methods, protocols and standards including, among others, token ring, Ethernet, Wireless Ethernet, Bluetooth, radio signaling, infra-red signaling, TCP/IP, UDP, HTTP, FTP, SNMP, SMS, MMS, SS7, JSON, XML, REST, SOAP, CORBA HOP, RMI, DCOM and Web Services.

According to some embodiments, the functions and operations discussed for producing a three-dimensional synthetic viewpoint can be executed on computer systems 402, 404 and 406 individually and/or in combination. For example, the computer systems 402, 404, and 406 support, for example, participation in a collaborative network. In one alternative, a single computer system (e.g., 402) can generate the three-dimensional synthetic viewpoint. The computer systems 402, 404 and 406 may include personal computing devices such as cellular telephones, smart phones, tablets, "fablets," etc., and may also include desktop computers, laptop computers, etc.

Various aspects and functions in accord with embodiments discussed herein may be implemented as specialized hardware or software executing in one or more computer systems including the computer system shown in FIG. 1. In one embodiment, computer system 402 is a personal computing device specially configured to execute the processes and/or operations discussed above. As depicted, the computer system 402 includes at least one processor 410 (e.g., a single core or a multi-core processor), a memory 412, a bus 414, input/output interfaces (e.g., 416) and storage 418. The processor 410, which may include one or more microprocessors or other types of controllers, can perform a series of instructions that manipulate data. As shown, the processor 410 is connected to other system components, including a memory 412, by an interconnection element (e.g., the bus 414).

The memory 412 and/or storage 418 may be used for storing programs and data during operation of the computer system 402. For example, the memory 412 may be a relatively high performance, volatile, random access memory such as a dynamic random access memory (DRAM) or static memory (SRAM). In addition, the memory 412 may include any device for storing data, such as a disk drive or other non-volatile storage device, such as flash memory, solid state, or phase-change memory (PCM). In further embodiments, the functions and operations discussed with respect to generating and/or rendering synthetic three-dimensional views can be embodied in an application that is executed on the computer system 402 from the memory 412 and/or the storage 418. For example, the application can be made available through an "app store" for download and/or purchase. Once installed or made available for execution, computer system 402 can be specially configured to execute the functions associated with producing synthetic three-dimensional views.

Computer system 402 also includes one or more interfaces 416 such as input devices (e.g., camera for capturing images), output devices and combination input/output devices. The interfaces 416 may receive input, provide output, or both. The storage 418 may include a computer-readable and computer-writeable nonvolatile storage medium in which instructions are stored that define a program to be executed by the processor. The storage system 418 also may include information that is recorded, on or in, the medium, and this information may be processed by the application. A medium that can be used with various embodiments may include, for example, optical disk, magnetic disk or flash memory, SSD, among others. Further, aspects and embodiments are not to a particular memory system or storage system.

In some embodiments, the computer system 402 may include an operating system that manages at least a portion of the hardware components (e.g., input/output devices, touch screens, cameras, etc.) included in computer system 402. One or more processors or controllers, such as processor 410, may execute an operating system which may be, among others, a Windows-based operating system (e.g., Windows NT, ME, XP, Vista, 7, 8, or RT) available from the Microsoft Corporation, an operating system available from Apple Computer (e.g., MAC OS, including System X), one of many Linux-based operating system distributions (for example, the Enterprise Linux operating system available from Red Hat Inc.), a Solaris operating system available from Oracle Corporation, or a UNIX operating systems available from various sources. Many other operating systems may be used, including operating systems designed for personal computing devices (e.g., iOS, Android, etc.) and embodiments are not limited to any particular operating system.

The processor and operating system together define a computing platform on which applications (e.g., "apps" available from an "app store") may be executed. Additionally, various functions for generating and manipulating images may be implemented in a non-programmed environment (for example, documents created in HTML, XML or other format that, when viewed in a window of a browser program, render aspects of a graphical-user interface or perform other functions). Further, various embodiments in accord with aspects of the present invention may be implemented as programmed or non-programmed components, or any combination thereof. Various embodiments may be implemented in part as MATLAB functions, scripts, and/or batch jobs. Thus, the invention is not limited to a specific programming language and any suitable programming language could also be used.

Although the computer system 402 is shown by way of example as one type of computer system upon which various functions for producing three-dimensional synthetic views may be practiced, aspects and embodiments are not limited to being implemented on the computer system shown in FIG. 4. Various aspects and functions may be practiced on one or more computers or similar devices having different architectures or components than that shown in FIG. 4.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A method of automatically generating a proposed response to user input comprising:
    receiving, via a text-based messaging system, a plurality of messages from a user;
    determining a respective confidence level for each message of the plurality of messages that the respective message has a respective intent corresponding to a respective defined intent;
    generating, responsive to the defined intent of a first message of the plurality of messages being a structured intent, a first proposed structured communication of a plurality of proposed structured communications from the structured intent;
    receiving a second message of the plurality of messages from the user;
    determining that the second message is not a valid response to the first proposed structured communication from the structured intent;
    generating, responsive to the defined intent of the second message being a predictive intent based on the determination that the second message is not a valid response to the first proposed structured communication, a first confidence level of the second message that the second message has the predictive intent meeting a pre-defined threshold, and the first confidence level that the second message has an intent corresponding to the predictive intent exceeding a second confidence level that the second message has an intent corresponding to the structured intent, a proposed predictive communication from the predictive intent; and
    generating a second proposed structured communication of the plurality of proposed structured communications to resume the plurality of proposed structured communications from the structured intent.

2. The method of claim 1, further comprising:
    responsive to the defined intent of the second message being the predictive intent, storing a state of a respective structured intent; and
    responsive to detecting a triggering event, restoring the state of the respective structured intent and generating the second proposed structured communication from the respective structured intent.

3. The method of claim 2, wherein detecting the triggering event is one of determining that a predetermined amount of time has passed, determining that a respective message has an intent corresponding to a topic, and determining that the respective message has an intent corresponding to the structured intent.

4. The method of claim 1, wherein generating the first proposed structured communication from the structured intent comprises:
    identifying a piece of information required by the structured intent; and
    responsive to determining that the piece of information has not previously been provided, generating the first proposed structured communication to request the piece of information from the user.

5. The method of any of claims 1, further comprising:
    generating, responsive to the defined intent of a third message of the plurality of messages being a predictive intent and the respective confidence level not meeting a second pre-defined threshold, a second proposed predictive communication from the predictive intent and presenting the second proposed predictive communication to a second user of the system.

6. The method of claim 5, further comprising receiving, from the second user, one of a first instruction to accept the second proposed predictive communication and a second instruction to reject the second proposed predictive communication.

7. The method of any of claims 5, wherein the user is a consumer, and the second user has expertise in a subject matter relevant to the consumer.

8. The method of claim 7, wherein the user is a caregiver to a patient, the second user is a medical professional, and the second proposed predictive communication relates to care of the patient.

9. The method of claim 1, wherein the user is one of a patient and a caregiver to a patient, and wherein the structured intent defines at least one clinical pathway for making a determination about the patient's health.

10. The method of claim 1, further comprising transmitting the first proposed structured communication and the proposed predictive communication to the user.

11. The method of claim 1, wherein the text-based messaging system comprises one of a native messaging application, a secure messaging application, a messaging application associated with a social media platform, and an SMS messaging application.

12. The method of claim 1, wherein determining the respective confidence level that a respective message has an intent corresponding to the defined intent is performed using at least one of a text-pattern matching process, a classification algorithm, and a neural network.

13. The method of claim 1, further comprising:
 determining, from a respective message, a piece of information about the user; and
 storing the piece of information about the user in one of a state machine and persistent storage.

14. A bimodal auto-response system comprising:
 an intent processor storing at least one structured intent and at least one predictive intent;
 a state machine storing at least one piece of information about a topic;
 a network interface configured to receive, over a communication network, a plurality of messages from a user;
 a predictive text classifier configured to:
  determine a respective confidence level that the intent corresponds to at least one intent of the at least one structured intent and the at least one predictive intent; and
  determine whether the respective confidence level that the intent corresponds to the at least one predictive intent meets a pre-defined threshold; and
 a rules engine configured to:
  generate a first proposed structured communication of a plurality of proposed structured communications responsive to determining that the at least one intent of a first message of the plurality of messages corresponds to a structured intent;
  generate a proposed predictive communication responsive to determining that the at least one intent corresponds to a predictive intent based on receiving a second message of the plurality of messages that is not a valid response to the first proposed structured communication, based on the respective confidence level that the at least one intent corresponds to the at least one predictive intent meeting the pre-defined threshold, and based on the respective confidence level that the at least one intent corresponds to the at least one predictive intent exceeding the respective confidence level that the at least one intent corresponds to the at least one structured intent; and
  generate a second proposed structured communication of the plurality of proposed structured communications to resume the plurality of proposed structured communications from the structured intent.

15. The system of claim 14, further comprising an API configured to receive information from at least one data source other than the state machine.

16. The system of claim 14, wherein the topic is a patient, and the at least one piece of information comprises longitudinal data about the patient.

17. The system of claim 14, wherein the intent processor further comprises a reentrant stack configured to store a state of at least one structured intent.

18. The system of claim 14, wherein the predictive text classifier is further configured to identify at least one part of speech in the message.

* * * * *